(12) United States Patent
Kettler et al.

(10) Patent No.: US 9,874,476 B2
(45) Date of Patent: *Jan. 23, 2018

(54) COLOUR RECIPE CALCULATING METHOD FOR MATT COLOUR STANDARDS

(71) Applicant: AXALTA COATING SYSTEMS IP CO., LLC, Wilmington, DE (US)

(72) Inventors: Wilhelm Kettler, Wuppertal (DE); Peter Jelen, Wermelskirchen (DE); Oliver Korten, Remscheid (DE)

(73) Assignee: AXALTA COATING SYSTERMS IP CO., LLC, Wilmington, DE (US)

( * ) Notice: Subject to any disclaimer, the term of this patent is extended or adjusted under 35 U.S.C. 154(b) by 704 days.

This patent is subject to a terminal disclaimer.

(21) Appl. No.: 14/360,926

(22) PCT Filed: Nov. 14, 2012

(86) PCT No.: PCT/US2012/065114
§ 371 (c)(1),
(2) Date: May 27, 2014

(87) PCT Pub. No.: WO2013/081833
PCT Pub. Date: Jun. 6, 2013

(65) Prior Publication Data
US 2014/0350895 A1    Nov. 27, 2014

Related U.S. Application Data

(60) Provisional application No. 61/563,881, filed on Nov. 28, 2011.

(51) Int. Cl.
*G01J 3/46* (2006.01)
*G01J 3/02* (2006.01)
(Continued)

(52) U.S. Cl.
CPC ............ *G01J 3/463* (2013.01); *G01J 3/0251* (2013.01); *G01J 3/46* (2013.01); *G01J 3/462* (2013.01);
(Continued)

(58) Field of Classification Search
CPC .. G01J 3/463; G01J 3/0251; G01J 3/46; G01J 3/462; G01J 3/504; G01N 21/4785; G01N 21/57
(Continued)

(56) References Cited

U.S. PATENT DOCUMENTS 5,003,500 A    3/1991   Gerber
5,231,472 A    7/1993   Marcus et al.
(Continued)

FOREIGN PATENT DOCUMENTS

EP         1631802 B1    8/2006

OTHER PUBLICATIONS

ISA European Patent Office, International Search Report and Written Opinion for International Application No. PCT/US2012/065114 dated Feb. 25, 2013.
(Continued)

*Primary Examiner* — Gregory J Toatley
*Assistant Examiner* — Douglas Kay
(74) *Attorney, Agent, or Firm* — Lorenz & Kopf, LLP

(57) ABSTRACT

The invention relates to a method for colour recipe calculation for matt colour standards with the steps: A) experimentally determining reflection spectra R(exp) of the color standard, comprising a first reflection spectrum (SPIN) and a second reflection spectrum (SPEX), with an integrating sphere color measurement instrument, wherein said first reflection spectrum (SPIN) is obtained at (A1) d/8°—geometry with the specular component included, and said second
(Continued)

reflection spectrum (SPEX) is obtained at (A2) d/8°—geometry with the specular component excluded; B1) calculating a recipe for the matt color standard based on the experimentally determined reflection spectrum R(exp) with the specular component included, which has been corrected for the specular component, or B2) comparing the experimentally determined reflection spectrum R(exp) with the specular component included, which has been corrected for the specular component, with reflection spectra associated to color recipes of a color recipe database for glossy color shades and identifying from said color recipe database a stored reflection spectrum which comes closest to the experimentally determined reflection spectrum R(exp) of the matt color standard, as well as the associated colour recipe; C) converting reflection spectra data of the experimentally determined reflection spectra (SPIN, SPEX) of the matt colour standard to gloss values, and D) converting the gloss values obtained to the amount of matting agent (MAA) with the assistance of previously prepared calibration curves for the available colorant system.

1 Claim, 10 Drawing Sheets

(51) Int. Cl.
| | | |
|---|---|---|
| | *G01J 3/50* | (2006.01) |
| | *G01N 21/47* | (2006.01) |
| | *G01N 21/57* | (2006.01) |

(52) U.S. Cl.
CPC .......... *G01J 3/504* (2013.01); *G01N 21/4785* (2013.01); *G01N 21/57* (2013.01)

(58) Field of Classification Search
USPC .......................................................... 702/289
See application file for complete search history.

(56) References Cited

U.S. PATENT DOCUMENTS

| | | | |
|---|---|---|---|
| 6,414,750 B2* | 7/2002 | Jung | G01J 3/18 356/328 |
| 7,158,672 B2* | 1/2007 | Johansson | G01J 3/0251 382/167 |
| 9,417,187 B2* | 8/2016 | Kettler | G01N 21/57 |

OTHER PUBLICATIONS

ISA European Patent Office, International Preliminary Report on Patentability for International Application No. PCT/US2012/065114 dated Jun. 12, 2014.

* cited by examiner

US 9,874,476 B2

COLOUR RECIPE CALCULATING METHOD FOR MATT COLOUR STANDARDS

CROSS-REFERENCE TO RELATED APPLICATION

This application is a U.S. National-Stage entry under 35 U.S.C. §371 based on International Application No. PCT/US2012/065114, filed Nov. 14, 2012 which was published under PCT Article 21(2) and which claims priority to U.S. Provisional Application No. 61/563,881, filed Nov. 28, 2011, which are all hereby incorporated in their entirety by reference.

FIELD OF THE INVENTION

The invention relates to a method for producing a colour recipe for a matt colour standard. The method can be used in the paint industry or other paint related fields.

DESCRIPTION OF RELATED ART

Efficiently matching colour shades of unknown pigmentation may be considered a significant problem for all colouristic applications in a coatings company. In particular in the vehicle coating sector, the variety of pigments has seen continuous expansion in recent years. In the light of this development establishing methods for minimising the effort needed for matching colour shades is of great economic importance.

Efficient matching of colour shades of unknown pigmentation in the colouristic is laboratory is now assisted by computer-based colour recipe calculation methods. The method of colour recipe calculation is a pigmentation analysis tool for colour shades making use of reflection spectroscopy in the visible wavelength range to characterise reflective properties of object colours and utilising a suitable radiative transport model to describe the diffusion of light in particulate media and thus the macroscopically detectable reflection spectra. The Schuster-Kubelka-Munk theory is often used for opaque and translucent pigmented solid surface coatings. Calculation of colour recipes generally involves making reference to pigment databases which administer details of optical properties of all pigments contained in available colorant systems. Reference may also be made to colour recipe databases, when only a correction of an already existing, but not perfectly matching, formulation is required.

Apart from glossy colour shades, matt-finished colour shades are also often used in colour-imparting surface coatings. Only few different methods of controlling the gloss-level of surface coatings are known so far. It is possible to matting a pigmented surface coating or to cover a glossy pigmented surface coating by a matt clear-coat layer. Adding a matting agent to a paint formulation is most frequently used to introduce the desired degree of surface texture to a polymeric material. These matting agents are homogeneously dispersed in the embedding medium; the effect of matting is achieved by some micro-heterogeneity inside the layer that produces an increase of diffuse light scattering from the sample surface. Different inorganic compounds as precipitated silica, kaolin, bentonite, or others serve as matting agents.

Since the determination of optical material parameters is a time- and cost-consuming procedure, it deems advantageous to formulate colour shades of different surface textures (glossy, semi-glossy, matt) using a common colorant database. In such a proceeding it is implicitly assumed that the characterization data determined for glossy colorants do not change very much when introducing some surface texture into the system, and that the resulting error in recipe calculation can be compensated by one or at most two additional correction steps. The time expenditure for the additional correction steps seems to be acceptable compared to the expenditure to determine optical material parameters for several colorant systems differing only by the degree of surface texture. In addition, working with only one colorant database provides the advantage of less stock-keeping units.

FIG. 4 displays details of the work flow of colour development process of matt-finished solid colour shades.

The current colour development or batch shading processes for matt-finished colour shades make use of two different instrumental approaches depending on whether an integrating sphere instrument or an instrument equipped with a collimated (directional) measurement geometry is utilised.

In case of the integrating sphere instrument (d/8° or 8°/d measurement geometry; FIGS. 1A and 1B) with a light source (1), a detector (2), a baffle (3) a white sphere cap or black trap (4), a sample (5), the difference spectrum $\Delta R = R$ (SPIN)−R(SPEX) between specular included (SPIN) and specular excluded (SPEX) readings is a function of surface gloss determined by the matting agent amount. Once this relation has been established by means of an appropriate set of calibration panels, the measured difference spectrum can be adopted to derive the matting agent amount (MAA) needed in a formulation to match a matt-finished colour standard.

In case of instruments equipped with a collimated measurement geometry (as, e.g., 45°/0°; FIG. 2), with a light source (1), a detector (2) over a sample (5) with illumination angles measured from the normal direction (z-z') of the sample surface, optimum colour recipe predictions can only be expected for colour standards with a gloss level above gloss≈30 units measured at the 60° geometry. In case of dull samples the spectrophotometer will pick up an undefined amount of surface gloss resulting in a sub-optimal prediction for the pigmentation. Below this limit the quality of predicted formulas deteriorates considerably with decreasing degree of surface gloss. A gloss-meter has to be utilised to establish a calibration function for the MAA=f(gloss) relation at the three different gloss geometries recommended in technical standards. These two methods of colour recipe calculation are disclosed in EP 1631802. The methods make reference to colour pigment and colour recipe databases for glossy colour shades which permit matt colour samples to be matched. For both methodical approaches the same set of calibration panels can be utilised to define the MAA=f (gloss) relationship. This set of panels should encompass several colour centres in colour space. The colour centres can, e.g., be represented by binary mixtures of coloured (blue, green, red, yellow, violet) and achromatic pigments (black, white). For each formulation a set of panels with increasing amount of matting agent has to be prepared, covering the entire range from perfectly glossy to totally matt.

The above methods still include a gap concerning the unification of the two approaches for integrating sphere instruments and spectrophotometers equipped with a collimated 45°/0° measurement geometry. A further disadvantage is that an additional gloss measurement device is necessary to obtain gloss values.

Accordingly there is still a need for a handy procedure for automating the colour development process and improving the results of recipe calculation of matt surface coatings which can be directly introduced and used in the colour development process.

Furthermore, there is a requirement for a colour recipe calculation method for matt colour standards which makes it possible, on the basis of a colorant system for producing glossy colour shades, to obtain acceptably accurate results without entailing additional tinting steps and in addition to obtain gloss values for the respective matt colour standard to be matched.

SUMMARY OF THE INVENTION

The present invention provides a method for colour recipe calculation of matt colour standards, in particular matt solid colour standards which makes use of general instrument profiles between an integrating sphere colour measurement instrument and a gloss measurement instrument equipped with three gloss-angle measurement geometries. These instrument profiles allow converting reflectance data to gloss information so that once the profiles are established the integrating sphere instrument would provide reflectance data and gloss data, i.e., the gloss-meter would be obsolete. The latter fact is particularly interesting for applications of distributed systems such as those running in refinish paint body shops to instrumentally support the car paint repair process. The necessary equipment can be reduced further and made more attractive from the pricing perspective. Also, processing time can be reduced generally in any application where the determination of reflectance data and gloss data is necessary.

The present invention accordingly relates to a method for producing a colour recipe of a matt colour standard, in particular a matt solid colour standard, the method comprising the steps of:

A) experimentally determining reflection spectra R(exp) of the colour standard, is comprising a first reflection spectrum and a second reflection spectrum, with an integrating sphere colour measurement instrument, wherein said first reflection spectrum is obtained at
(A1) d/8°—geometry or 8° d—geometry with the specular component included, and said second reflection spectrum is obtained at
(A2) d/8°—geometry or 8° d—geometry with the specular component excluded;
B1) calculating a recipe for the matt colour standard based on the experimentally determined reflection spectra R(exp) by conventional recipe calculation method, wherein the experimentally determined reflection spectrum R(exp) with the specular component included (1), which has been corrected for the specular component, is matched by using the optical material parameters of the pigments of an available colorant system for the preparation of glossy colour shades, so obtaining a colour recipe specifying the nature of the pigments and the concentrations thereof, or
B2) comparing the experimentally determined reflection spectrum R(exp) with the specular component included (1), which has been corrected for the specular component, with the reflection spectra associated to colour recipes of a colour recipe database for glossy colour shades and identifying from said colour recipe database a stored reflection spectrum which comes closest to the experimentally determined reflection spectrum R(exp) of the matt colour standard as well as identifying the associated colour recipe;
C) converting reflection spectra data of the experimentally determined reflection spectra R(exp) of the matt colour standard to gloss values by:
C1) acquiring the difference reflection spectrum $\Delta R$ of the experimentally determined reflection spectrum R(exp) with the specular component included (1) and the experimentally determined reflection spectrum R(exp) with the specular component excluded (2), and
C2) determining the gloss values corresponding to said difference reflection spectrum $\Delta R$ with the assistance of previously prepared calibration curves whose curves represent the functional relationship between the difference reflection spectrum $\Delta R$ and the gloss values measured at one or more gloss angles,
D) producing the colour recipe for the matt colour standard by converting the so obtained gloss values to the amount of matting agent with the assistance of previously prepared calibration curves for the available colorant system, whose curves represent the gloss values measured at one or more gloss angles as a function of the amount of at least one matting agent in colour recipes.

It goes without saying that all data, for example, the colorant system and the data associated therewith, e.g. the optical material parameters, and the previously prepared calibration curves for the available colorant system (as used in steps C2) and D)), are preferably stored in a database.

Figure 8A:
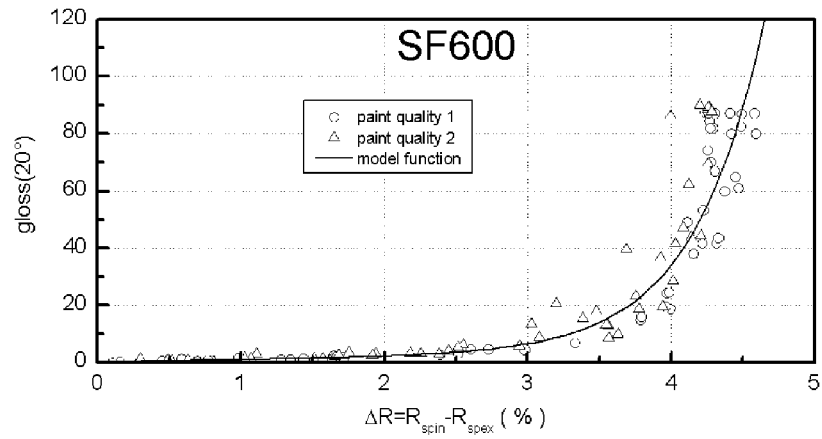
Figure 8B:
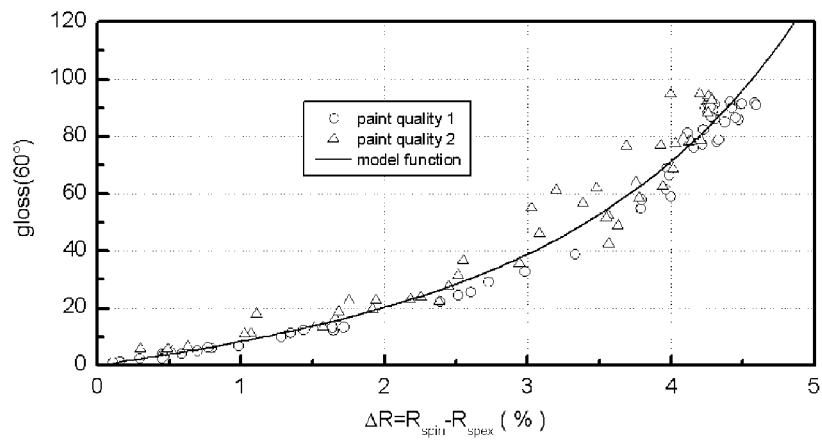
Figure 8C:
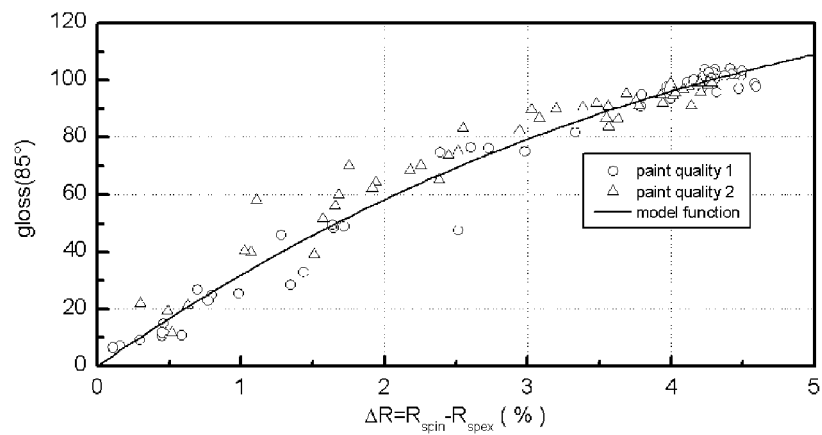
Figure 9A:
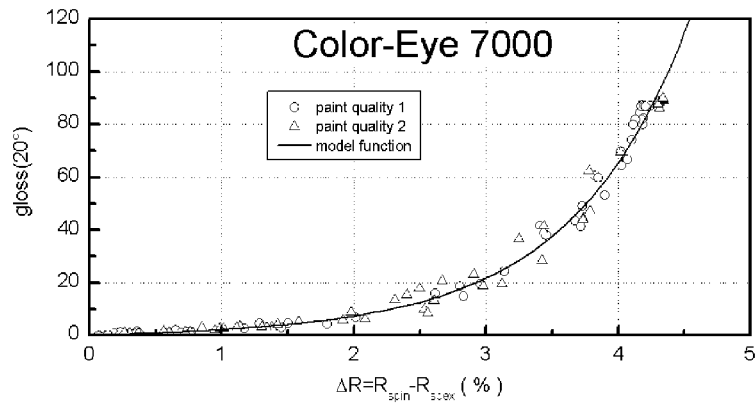
Figure 9B:
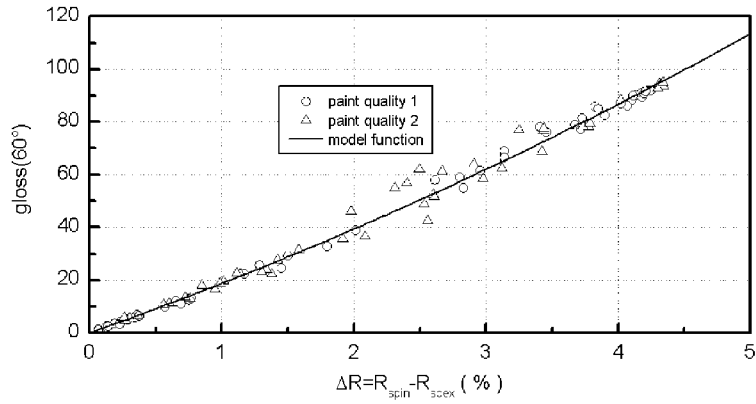
Figure 9C:
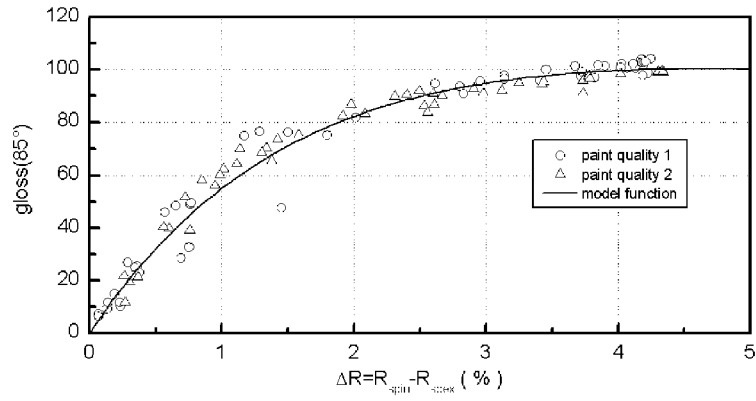

The gloss values have been measured with the micro TRI-gloss instrument of Byk-Gardner. The reflectance data have been measured with the colour measurement instrument SP64 of X-Rite (FIG. 7), with the colour measurement instrument SF600 of Datacolor International (FIG. 8), and with the colour measurement instrument Color-Eye 7000 of Gretag-Macbeth (FIG. 9).

Figure 10:
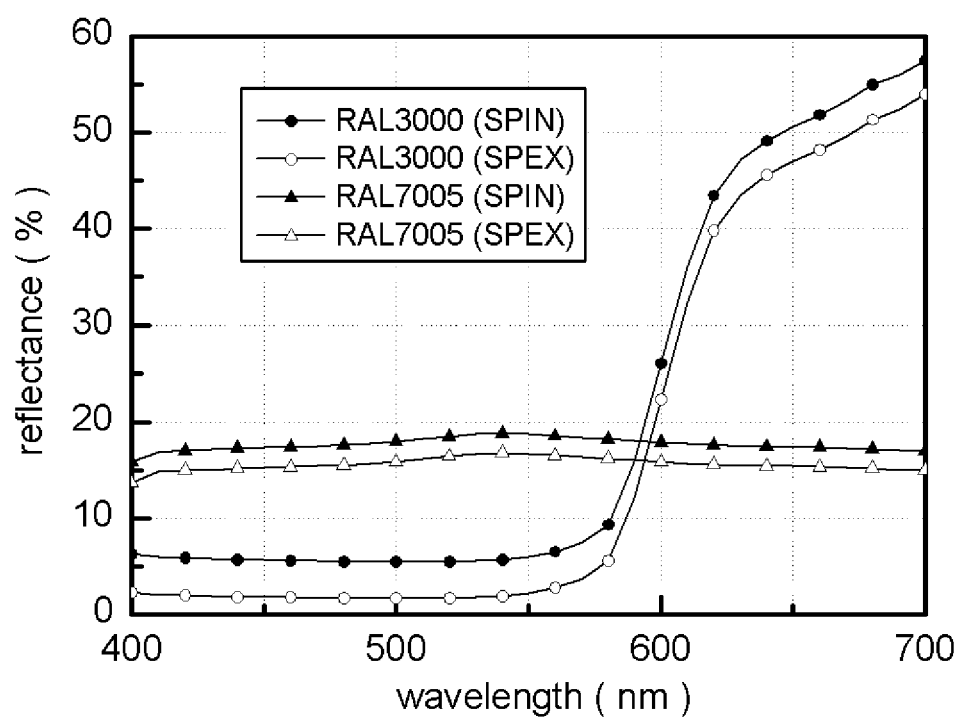

FIG. 10 displays the experimental reflectance functions of two semi-glossy RAL colours 3000 and 7005 with the visible spectral range. Reflectance data have been obtained by means of an integrating sphere instrument with measurement geometry d/8° operated in the specular included (SPIN) and excluded (SPEX) modes.

Figure 11:
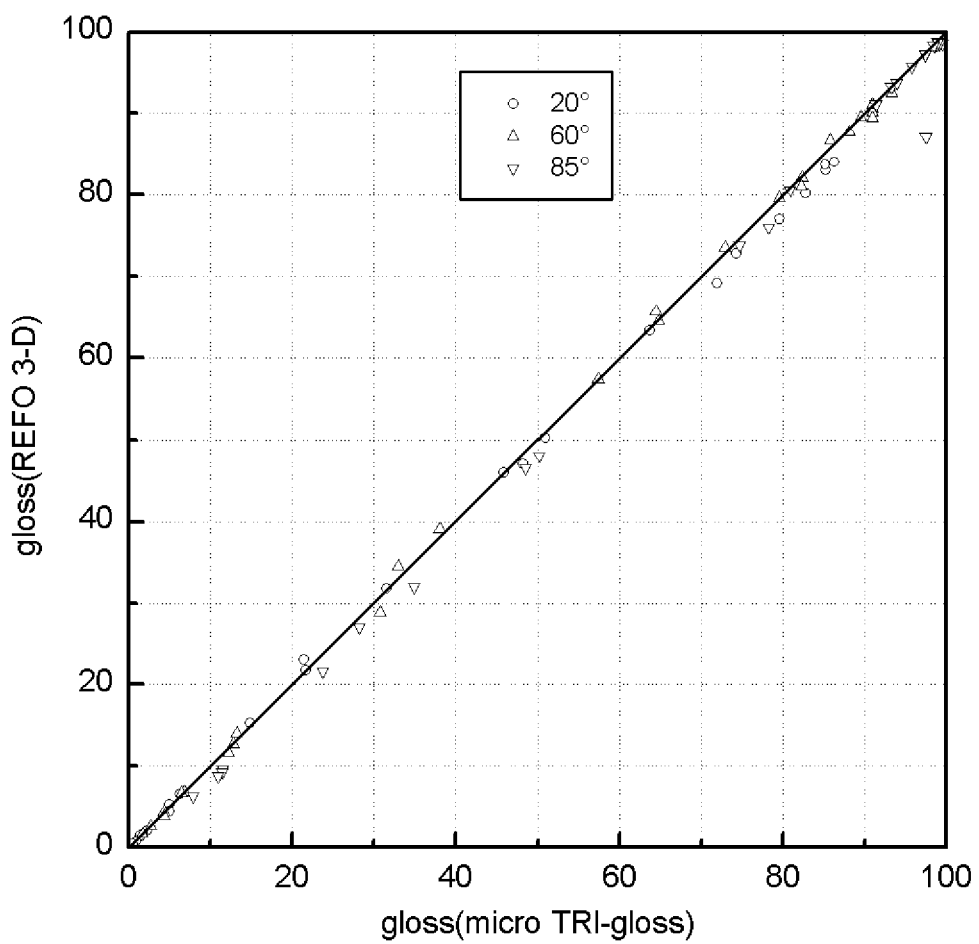

FIG. 11 illustrates the correlation of gloss data obtained by means of two instruments of different manufacturers (micro TRI-gloss of Byk-Gardner and REFO 3-D of Hach Lange GmbH) at all three assessment geometries. The correlation index r, at all assessment geometries exceeds a value of 0.999 indicating that the instrument scales of both instrument are congruent.

DETAILED DESCRIPTION OF THE EMBODIMENTS

These and other features and advantages of the present invention will be more readily understood, by those of ordinary skill in the art, from a reading of the following detailed description. It is to be appreciated that those certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

"Colour standard" shall mean herein and in the following any coated or is coloured surface for which gloss values are to be determined. A colour standard can be a cured or dried paint layer, a wet paint layer, an inherently coloured surface of a substrate or any other coloured substrate of arbitrary character. When measuring the reflectance spectrum of wet paint films typical methods and devices for measuring wet paint films can be used. The colour standard can be, for example, a surface of a substrate to be repair coated or a part thereof, in particular the coated surface of a car body to be repair coated, or a part thereof. The colour standard comprises colour standards with different surface gloss. It includes glossy and matt colour standards, solid colour standards, effect colour standards and combinations thereof.

"Matt colour standard" shall mean herein and in the following any colour standard which does not have a perfectly glossy surface. The initial gloss of a colour shade can be decreased to a desired gloss value, for example, by adding one or matting agents to the paint composition creating the matt colour standard. The matt colour standard can be a matt solid colour standard or a matt effect standard. The matt colour standard also includes so-called semi-gloss colour standards.

"Solid colour standard" shall mean herein and in the following a colour shade or colour standard with optical property of isotropically reflecting a beam of collimated or diffuse incident light. If, e.g., such a colour shade is illuminated by a collimated beam of light at a constant angle, the level of the reflected light and with it the colour will be independent on the viewing angle. Such colour shades can be formulated by means of solid pigments or dyes which may be embedded and dispersed in different media like paint, ceramic, glass, or plastic etc.

"Solid pigment" shall mean herein and in the following an inorganic or organic substance consisting of small particles which are practically insoluble in the applied medium and used owing to their colouring, protective, or electromagnetic properties. Solid pigments can be characterised by their chemical composition and their optical and technical properties. Their optical properties are determined by their light scattering and absorbing properties which can be selective (coloured pigments) or aselective (black and white pigments).

"Colorant system" shall mean herein and in the following any system of solid and/or effect pigments, comprising all pigments which shall be used for the production or formulation of paints. The number and choice of pigment components are not subject to restrictions here. They may be adapted in any manner to the relevant requirements, e.g., according to the requirements of the paint manufacturer is or its customers.

The term "matt solid colour standard" can be used here and in the following interchangeably with the terms "matt solid colour sample" and "matt solid colour shade" and "matt colour standard having a solid colour".

The term "matt colour standard" can be used here and in the following interchangeably with the terms "matt colour sample" and "matt colour shade".

The principle and the individual steps of the method according to the invention are explained in greater detail below. The method of the present invention is preferably a method for colour recipe calculation of matt solid colour standards. Therefore, here and in the following the term matt solid colour standard is used. However, it goes without saying that the method of the present invention also includes a method for colour recipe calculation for matt effect colour shades and that the individual steps and features explained in greater detail below are also related to a method for colour recipe calculation of matt effect colour shades.

The starting point is a matt solid colour standard which is to be matched or for the matching of which a suitable colour recipe is to be developed.

First of all, in accordance with step A) of the method according to the invention, the reflection spectra R(exp) of the matt solid colour standard are experimentally determined over a defined wavelength range with the help of a suitable colour measurement instrument equipped with a d/8° measurement geometry. The reflection spectra are preferably determined over a wavelength range of 400-700 nm. The reflection spectra are measured at d/8° or 8°/d geometry with the specular component included (A1) and at d/8° or 8°/d geometry with the specular component excluded (A2).

It goes without saying and is well known to a person skilled in the art that an integrating sphere colour measurement instrument can be equipped with a d/8° measurement geometry or alternatively with a 8°/d measurement geometry since both measurement geometries are equivalent measurement geometries. Therefore, if in the following only the term "d/8° measurement geometry" is used the equivalent 8°/d measurement geometry is also meant and can also be used.

Figure 1A:
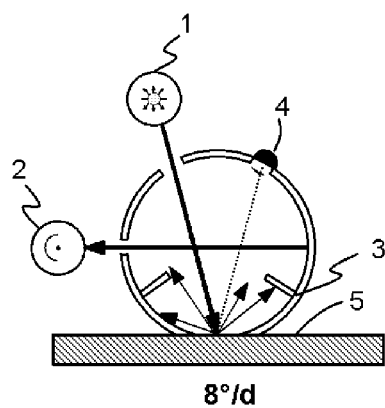
FIG. 1 illustrates the standard d/8° and 8°/d measurement geometries, respectively, recommended by technical standards (as, e.g., DIN 5033) to be used for glossy and matt solid colour standards.
Figure 1B:
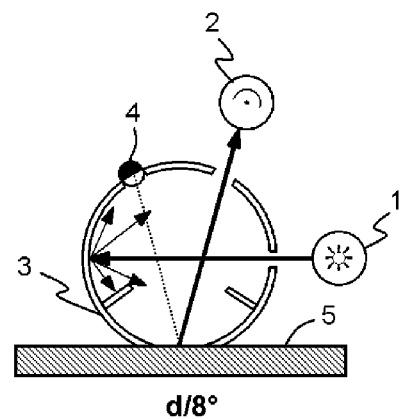
Figure 2A:
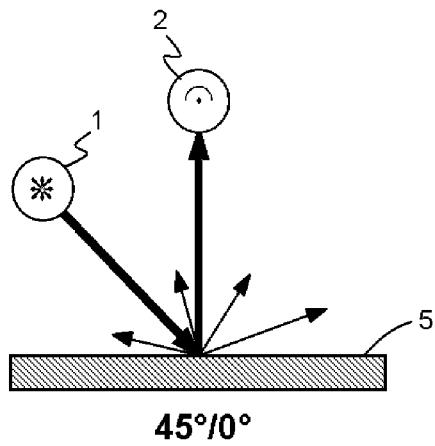
FIG. 2 illustrates standard 45°/0° and 0°/45° measurement geometries, respectively, recommended by technical standards (as, e.g., DIN 5033) to be used for glossy and matt solid colour standards.
Figure 2B:
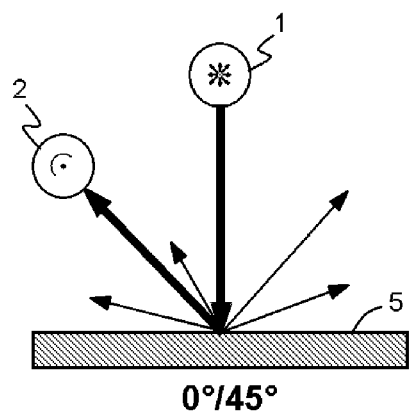

The d/8° measurement geometry is based on diffuse illumination (by means of an Ulbricht sphere) and directional observation at an angle of 8° with respect to the is surface normal (d/8°) of a sample (as illustrated in FIG. 1). In the present case of matt solid colour samples, two measurements can be made operating the instrument in the specular included and excluded modes.

D/8° measurement geometries, e.g. according to the one depicted in FIG. 1 are exhaustively described in the specialist literature, are familiar to the person skilled in the art of colour measurement, and are implemented in known conventional measurement instruments. Moreover, the measurement geometries are defined and recommended, e.g., in technical standard DIN 5033 (Farbmessung) or CIE publication 15.3 (colorimetry).

Optionally, e.g., if required for further processing, the colour positions (X, Y, Z, or L*, a*, b*) may be determined or measured in a conventional manner known to the person skilled in the art of colour measurement. The colour positions may be determined on the basis of the experimentally determined reflection spectrum of the matt solid colour standard for both specular included and excluded data sets. The colour positions may also be measured with an appropriate measuring device. The colour positions may then be used in the following process steps instead of or in addition to the reflection data.

Depending upon which initial database is accessed, the next step of the method according to the invention involves either B1) calculating a recipe for the matt solid colour standard based on the experimentally determined reflection spectra R(exp) by usual recipe calculation method, wherein the experimentally determined reflection spectrum R(exp) with the specular component included (A1), which has been corrected for the specular component, is matched by using the optical material parameters of solid pigments of an available colorant system for the preparation of glossy colour shades, so obtaining a colour recipe specifying the nature of the pigments and the concentration thereof, or B2) comparing the experimentally determined reflection spectrum R(exp) with the specular component included (1), which has been corrected for the specular component with the reflection spectra associated to colour recipes of a colour recipe database for glossy colour shades and identifying from said colour recipe database a stored reflection spectrum which comes closest to the experimentally determined reflection spectrum R(exp) of the matt solid colour standard, as well is as identifying the associated colour recipe.

Step B1) or B2) of the method according to the invention proceed in accordance with the art using pigment databases, e.g. discrete solid pigment (colouring pigment) databases or colour recipe databases containing the required optical material parameters of the pigments of the available colorant system. It is advantageous that it is possible to access colorant systems or colour recipes as are used for producing glossy colour shades.

Only the specular included reading (experimentally determined reflection spectrum R(exp) with the specular component included (A1)) is utilised for the recipe prediction calculations, after subtracting the surface gloss from the experimental data (corrected for the specular component). The surface gloss can either be derived from the known refractive index of the embedding medium or determined experimentally in advance. In the former case the gloss contribution can be estimated by means of the Fresnel formula for unpolarised light which for light incident almost perpendicularly to the sample surface reduces to $$\Delta R = R(SPIN) - R(SPEX) = \left(\frac{n-1}{n+1}\right)^2$$

with n denoting the refractive index of the embedding medium. For n≈1.5 a value of ΔR=0.04 is obtained. An experimental approach to determine the gloss contribution to the measurement signal is to prepare a very dark (or black) glossy colour shade in the paint quality in question and to measure the difference spectrum $\Delta R(\lambda) = R(\lambda, SPIN) - R(\lambda, SPEX)$, which in all subsequent calculations serves as a spectral gloss correction. The spectra from which the specular component has been eliminated may then be formulated as usual with the data set of optical material parameters determined for a set of glossy calibration panels.

The optical material parameters describe the scattering and absorbing properties of the coloured pigments when dispersed in the particular binder system. The parameters are pigment-specific and wavelength-dependent and must be determined at each desired wavelength by means of a set of appropriate calibration panels. To this end, a specific set of opaque calibration panels is produced for each colouring pigment and the reflection spectra are measured at the desired illumination and observation geometry. The optical material parameters are determined by fitting the adopted radiative transport model to the reflection factors experimentally determined is for each pigment or pigment mixture. In case of the present solid colouring pigments, the known Schuster-Kubelka-Munk approximation to the radiative transport equation or its variants is sufficient for the described purpose. Using this approximation, it is possible to derive a simple relationship between the reflection R of an opaque surface coating and the scattering (S) and absorption properties (K) of the colouring pigments contained in said coating. The scattering and absorption coefficients are here obtained by adding together the individual contributions, weighted for the particular concentration, made by the various different colouring pigments.

Alternatively, according to step B2) the spectrum from which the specular component has been eliminated may be used as usual to identify the appropriate reflection spectrum and the colour recipe associated with it from a colour recipe database.

After having carried out step B1) or B2), it is possible, if necessary, to correct the calculated or identified colour recipe and to adjust the obtained matt solid colour standard based on the colour recipe calculated or identified in the first matching step to the desired matt solid colour standard. Correction steps can be repeated until the obtained matched matt solid colour standard is within a requested tolerance.

In step C) of the method according to the invention the reflection data of the experimentally determined reflection spectra R(exp) of the matt solid colour standard are converted to gloss values.

This requires first (step C1) acquiring the difference reflection spectrum ΔR of the experimentally determined reflection spectrum R(exp) with the specular component included (A1) and the reflection spectrum R(exp) with the specular component excluded (A2). Then in step C2) the gloss values corresponding to said difference reflection spectrum ΔR are determined with the aid of previously prepared calibration curves, whose curves represent the functional relationship between the difference reflection spectrum ΔR and the degree of surface gloss.

The determination of the functional relationship between the difference reflection spectrum ΔR and surface gloss will be explained below in more detail.

Preparation of Calibration Panels

The colour shades to be used to generate the gloss=f(ΔR) profiles have to cover the entire range of gloss levels, if well-performing gloss=f (ΔR) model functions shall be established. It is not the number of samples which is important for the model building, but rather a uniform distribution of gloss levels in the sample set. In order to generate is the gloss=f(ΔR) profiles (calibration curves) the new preparation of a special set of calibration panels may not be needed if history data (gloss data and R(exp) with specular component included and excluded) are already available. If such a sample set of history data is not available, a special set of calibration panels needs to be prepared which later can be augmented by additional history data. Basis for preparing the calibration panels is the available colorant system.

In order to keep the number of calibration panels as low as possible and high enough to achieve the envisaged accuracy and to be representative for the respective paint mixing system and related colour system, panels have to be prepared only for a subset of pigments. Such a subset may comprise black, white, red, green, blue, yellow and violet pigments, where the coloured pigments are blended with the white mixing paint of the paint system, while the neutral pigments are used as masstones. One-layer top coat systems already form glossy surfaces, while in case of two-layer top coat systems (base coat+clear coat) the pigmented base-coat has to be covered by a glossy clear-coat. This set of panels defines the glossy end of the ladder of surface texture. All of these formulas have to be blended with a matting agent (in case of one-layer top coat systems) or covered by a matted clear-coat (in case of two-layer top coat systems) to adjust the desired level of surface gloss. For each paint system generally a natural upper limit for the addition of matting agent to the base-coat or clear-coat exists, which will define the second extreme matt end of the ladder of surface texture. The glossy variant will assume gloss values of the order of 90-100 units, while gloss-values of the other extreme of matt-finished variant will be of the order of less than 5 units. These two extreme points of the ladder of surface texture have to be supplemented by N further calibration panels with gloss values almost equally spaced between the two extreme points. Preparation of, for example, N=4 to 6 panels per pigment of varying gloss level will be sufficient for the definition of a well-balanced calibration echelon.

In a well-behaved paint system preparation of calibration panels for a single pigment would be sufficient to define a generalized instrument profile. This ideal situation is barely met in practical applications of one-layer top coat paint systems. Integration of pigments into the boundary layer between paint and air will have an impact on the surface gloss and add coloured contributions to the regularly reflected neutral gloss component. Hence, even if the same amount of matting agent is used in different is colour formulas the corresponding surface gloss level may vary considerably.

An alternate approach for the definition of generalized instrument profiles can be taken if a sufficiently high number of history data sets of previously developed matt-finished colour shades is available. Plotting surface gloss values versus the difference measure of specular included and excluded reflectance spectra at each gloss assessment geometry will also provide calibration curves if the paint system is well-behaved and a good correlation between both quantities exists.

The calibration curves are generated for a specific pair of instruments: the colour measurement instrument and the gloss measurement instrument.

Gloss Measurement

For the instrumental gloss characterisation collimated measurement geometries have been recommended in technical standards. In case of glossy samples the light partially reflected at the air/paint interface follows the reflection law (angle of reflection=angle of illumination) and can be quantitatively described by Fresnel's equations. The intensity of the reflected light depends on the angle of the incident light and the optical material properties (complex refractive index). The component refracted into the medium undergoes selective absorption and scattering when interacting with the embedded pigment particles and is almost diffusely reflected from the layer. This diffusely reflected light likewise contributes to the specularly reflected component and therefore also has an effect on gloss perception. In case of textured surfaces the light reflected from the surface can be divided into a specular and a diffuse reflected component. With increasing degree of surface roughness the energy of the specularly reflected component will steadily decrease and progressively contribute to the diffusely reflected component.

Figure 3:
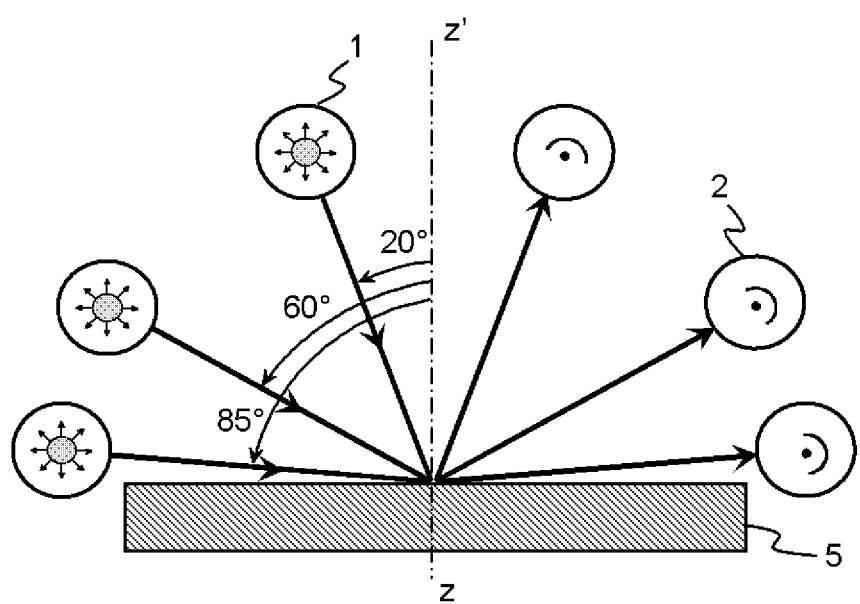
FIG. 3 displays the recommended geometrical conditions for the measurement of surface gloss.
Figure 4:
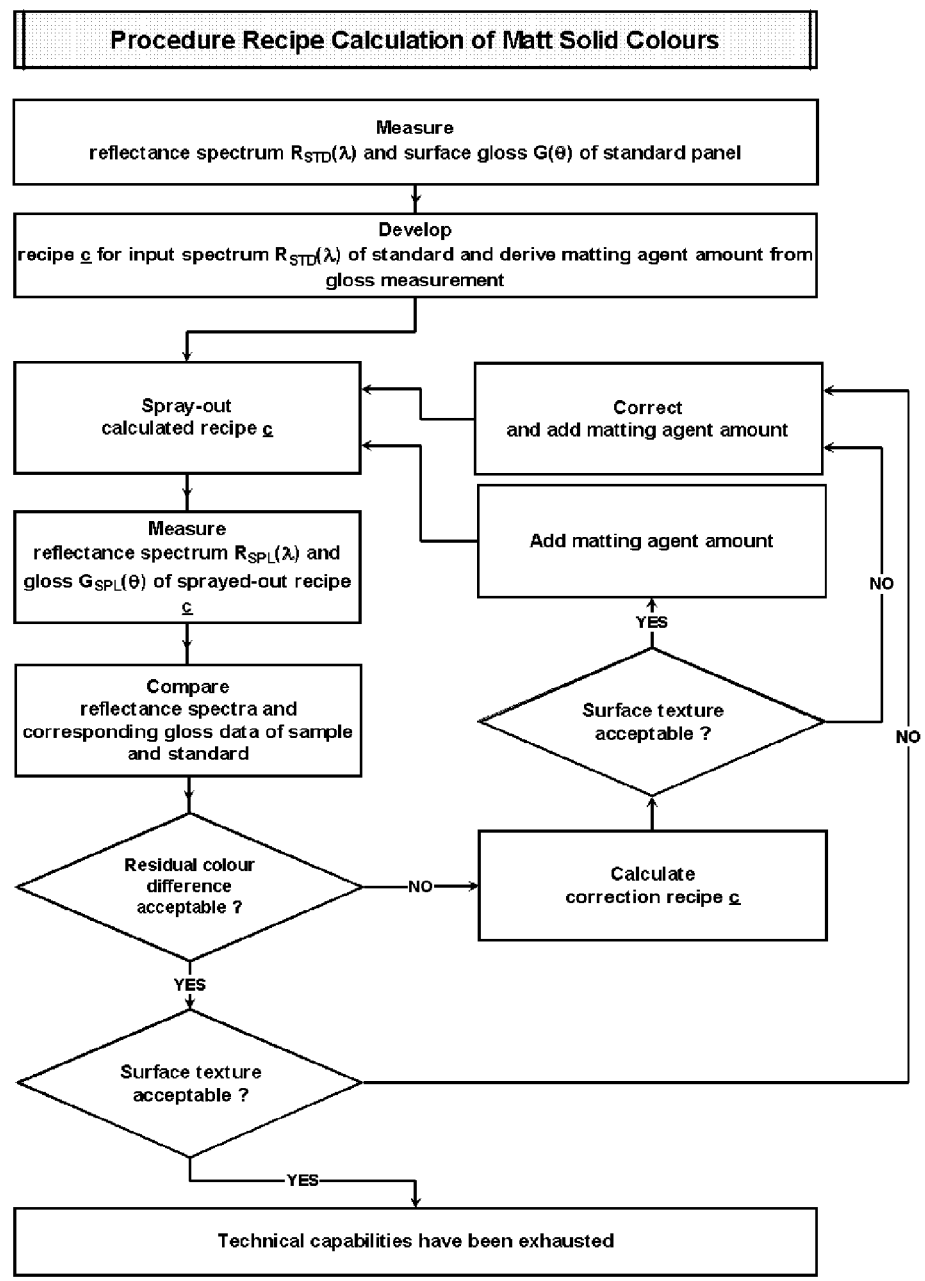
FIG. 4 shows the procedure of recipe calculation of matt solid colours.

Surface gloss is experimentally determined by means of an appropriate reflectometer according to technical standards DIN 67530 or ASTM D 523-89, defining the experimental conditions to instrumentally assess surface gloss. Within the technical standard three different measurement geometries are recommended to characterise the surface gloss at 20°, 60°, and 85° with respect to the surface normal (see FIG. 3). The 20° angle is used to characterise glossy samples, the 60° angle is recommended for semi-glossy samples, and the 85° angle is supposed to provide reliable information for matt samples.

The measured reflectometer values are referred to the corresponding values of a glossy black glass having a refractive index of n=1.567. The black glass has an assigned specular gloss value of 100 for each measurement geometry. Since none of the recommended measurement angles will provide results of highest accuracy for all gloss levels (see FIG. 3) the first step in determining the gloss level of a specimen is to identify the appropriate measurement geometry. If the 60° gloss value is between 10 and 70 units, this is supposed to be the correct measurement geometry. If the 60° gloss is lower than 10 units, the 85° geometry should be used instead, while the 20° geometry result will be advantageous for comparison in case the 60° value exceeds the 70 units boundary. Consequently, there are two discontinuities in the gloss scale which can only be defused by some kind of averaging of the gloss values obtained at the three measurement geometries.

Gloss data obtained by different instruments of different manufacturers are generally commensurable within the experimental errors if their design follows the guidelines recommended in the above-mentioned technical standards. In order to demonstrate the validity of this assertion a set of matt-finished panels of varying degree of surface texture has been measured on two different gloss-meters of different manufacturers (micro TRI-gloss of Byk-Gardner, REFO 3-D of Hach Lange GmbH) for a quantitative comparison. All experimental data obtained are collected in FIG. 11. As can be seen from FIG. 11, all gloss data experimentally determined for both types of gloss-meters are highly correlated with a correlation index of $r_c$>0.999 at all three assessment angles. Within the experimental errors at least these two instrument types can be exchanged without expecting a break in gloss scales which are congruent. Therefore, only gloss data of the micro TRI-gloss instrument of Byk-Gardner have been adopted for all numerical analyses.

Generalised Gloss Profiles

Figure 7A:
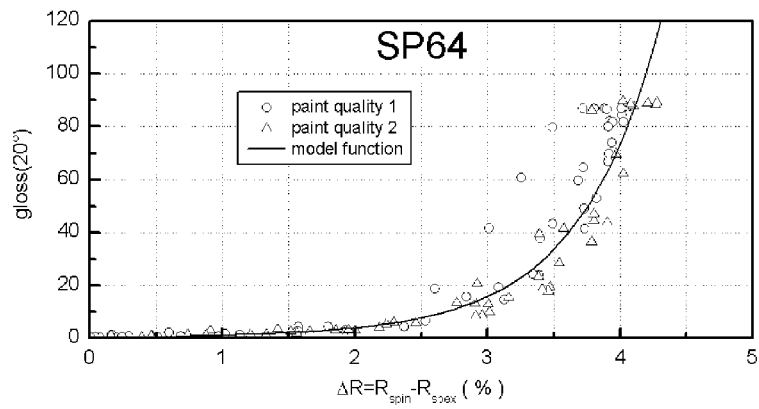
FIGS. 7 to 9 show gloss profiles obtained for three typical integrating sphere colour measurement instruments for the three angle geometries (20°, 60°, and 85°) recommended by technical standards to access surface gloss of matt-finished surface coatings. The continuous curves through the data points represent fits to is appropriate model functions. The experimental data sets have been obtained for two different paint systems (paint quality 1 and paint quality 2). Both paint systems represent solvent-based Refinish mixing systems, where paint quality 1 is a balanced quality and paint quality 2 a concentrated quality (pastes). In the latter case formulas have to be completed by the addition of an appropriate amount of binder.
Figure 7B:
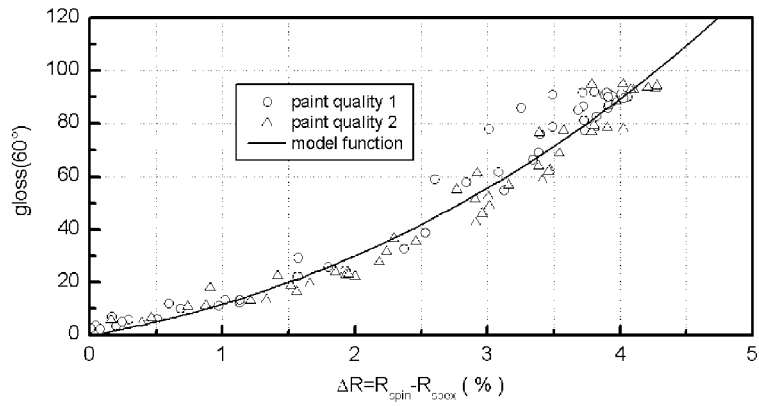
Figure 7C:
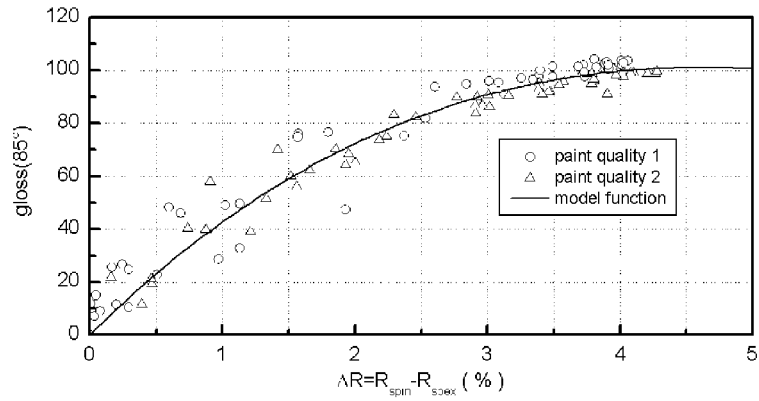

Both gloss and colour readings can be combined in three mathematical models relating gloss data obtained at the three recommended different gloss geometries (20°, 60°, and 85°) to the spectral difference ΔR=R(SPIN)−R(SPEX) determined by means of an integrating sphere instrument. FIG. 7 displays experimental data obtained for carefully chosen sets of calibration panels of two different refinish mixing systems along with model functions fitted to the experimental data. Obviously all sets of data are well-behaved and follow universal functions at all three measurement is geometries. The functional behaviour can be approximated by a single non-linear model function having only three parameters which have to be adjusted at each gloss angle geometry in the sense of the $L_2$-norm by means of an efficient non-linear fitting routine minimising the sum of weighted squares of residuals between model function and experimental data. The parameter sets depend on the spectrophotometer type utilised for the collection of spectral data. This dependence is a consequence of the fact that each instrument manufacturer uses his own integrating sphere with design parameters chosen for optimum performance of the respective instrument. Size of the sample port and gloss trap, efficiency of the gloss trap, as well as apertures of the optical system will have an impact on the measurement results. The derived gloss profiles can be used to compute gloss values for all three gloss angles for a given difference reflection spectrum ΔR of the experimentally determined reflection spectrum R(exp) with the specular component included (A1) and the experimentally determined reflection spectrum R(exp) with the specular component excluded (A2).

The performance of the approach of generalized instrument profiles is illustrated below using the example of different types of spectrophotometers of three instrument manufacturers: SP64 of X-Rite, Color-Eye 7000 of Gretag-Macbeth, and SF600 of Datacolor International. All of these instruments are equipped with integrating Ulbricht spheres which can be operated in specular included and specular excluded modes. However, the geometrical size and design of apertures is different for each of these Ulbricht spheres so that for colour standards of varying gloss level different experimental results for the difference ΔR=R(SPIN)×R(SPEX) have to be expected.

In order to define generalized instrument profiles two sets of matt-finished calibration panels of varying gloss levels of two different paint systems have been prepared and measured on all three instruments. Both paint systems represent solvent-based Refinish mixing systems, where paint quality 1 is a balanced quality and paint quality 2 a concentrated quality (pastes). The surface gloss of the entire set of calibration panels has been characterized by means of a micro TRI-gloss instrument of Byk-Gardner (see FIGS. 7-9).

With other words, the unification of the approaches based on the directional 45°/0° and diffuse d/8° measurement geometries has been accomplished by establishing general instrument profiles between an integrating sphere instrument and a gloss-meter relating the difference spectrum ΔR=R(SPIN)−R(SPEX) to the gloss information derived at the three recommended gloss-geometries. Therefore, three instrument profiles have to be created. Based on readings taken on an appropriately chosen set of matt-finished calibration panels of variable level of surface gloss and independent gloss measurements, calibration curves (profiles) can be generated relating the difference spectrum ΔR=R(SPIN)−R(SPEX) to the gloss values obtained at the three standard measurement geometries. These calibration curves are independent of the paint quality chosen (if the paint quality is well-behaved and will not integrate pigment particles into the airpaint interface) and only depend on the optical details and configuration of the hardware used (spectrophotometer, gloss-meter). For each pair of instruments—colour measurement instrument and gloss measurement instrument—individual instrument profiles have to be generated.

The gloss information obtained in step C2) can subsequently be fed into the gloss profile converter relating surface gloss and matting agent amount, to derive the matting agent amount needed to match a matt solid colour standard.

Therefore, in step D) of the present invention the quantity of matting agent corresponding to the determined gloss values in the matt solid colour standard is determined with the assistance of previously prepared calibration curves for the available colorant system. The calibration curves were prepared by previously measuring the degree of gloss at one or more gloss angles on calibration panel sets containing differing quantities of matting agents and plotting the degree of gloss as a function of matting agent concentration.

Should various matting agents or mixtures of matting agents be used in the available colorant system, corresponding calibration curves must be produced for each matting agent and each matting agent mixture. Further details of this step are disclosed in EP 1631802.

The colour recipe obtained in B1) or B2) and the determined quantity of matting agent may be output separately or the determined quantity of matting agent is directly suitably incorporated into the previously determined colour recipe. In the latter case the quantity of matting agent obtained in step D) is combined with the colour recipe obtained in step B1) or identified in step B2), so obtaining a colour recipe to match the matt solid colour standard, whose recipe contains the nature of the colour-imparting pigments and the concentrations thereof and in addition the amount of matting agent.

Obviously, when performing steps A) to D) of the method according to the invention, the stated sequence is not mandatory, but can be changed according to the knowledge of a person skilled in the art. For example, after having performed step A) it is accordingly possible to perform first steps C) and D) (determination of degree of gloss and determination of matting agent concentration) and subsequently to perform step B1) or B2) (calculate or identify colour recipe). The recipe and the amount of matting agent can be determined independently from each other. Usually the necessary calibration curves are prepared in advance based on the components of the available colorant system and available matting agents, and are stored and maintained in a database. So if actually a new matt solid colour standard has to be matched the calibration curves and related data and models do already exist defining the instrument profile.

Moreover, any optionally required correction of the colour shade produced with the determined colour recipe as calculated in step B1) or identified in step B2) may also be performed until after the complete recipe, including the matting agent content, has been obtained. It is likewise obvious that the obtained degree of gloss/matting may, if necessary, also be corrected by adjusting the matting agent concentration.

Figure 6:
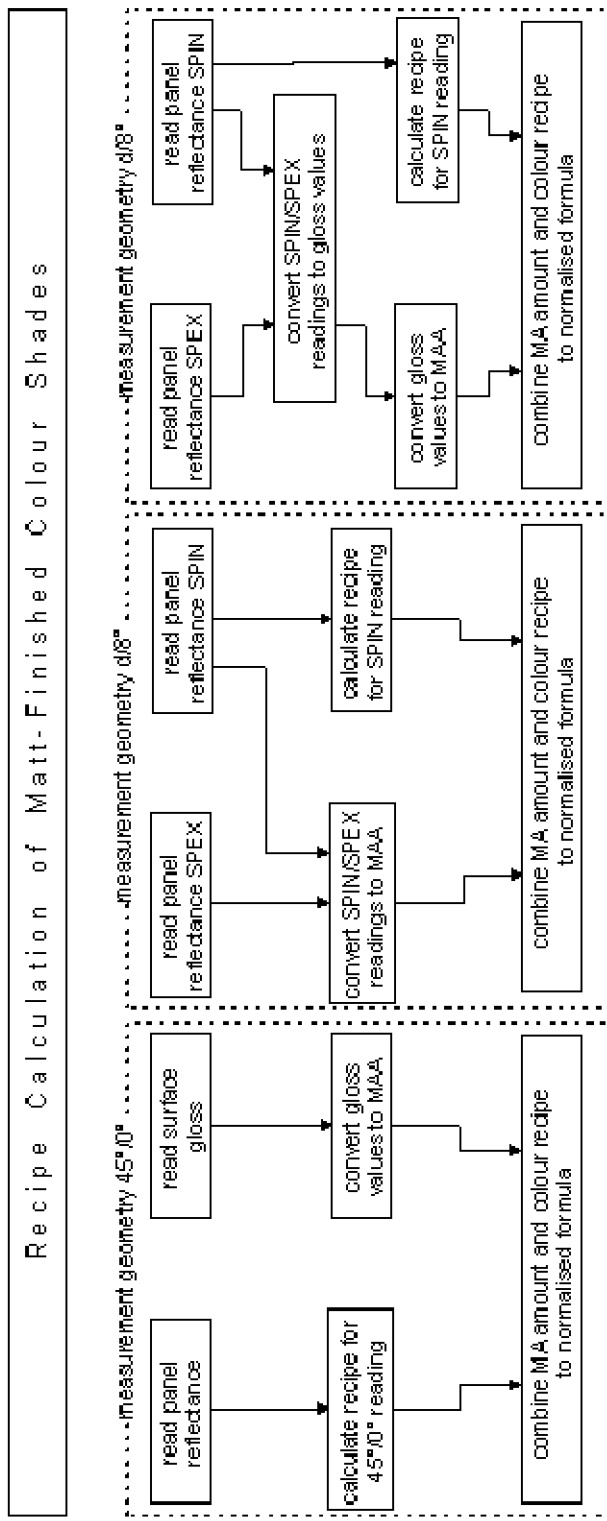
FIG. 6 shows the process flow chart of recipe calculation procedure of matt-finished colour shades for the two standard measurement geometries 45°/0° (left part of diagram; MAA=matting agent amount) and d/8° (middle part of diagram). The right diagram displays the new process flow when converting spectral data to gloss values, before converting these gloss values to a matting agent amount.

The process flow for the known approaches to recipe prediction of matt-finished colour shades and the new approach of the present invention is depicted in FIG. 6, i.e. the known process with measurement geometry 45°/0° with gloss measurement; the known process with measurement geometry d/8° without gloss measurement and without obtaining gloss values; and the method of the present invention with measurement geometry d/8° and without gloss measurement, but with obtaining gloss values.

Useful matting agents comprise conventional products, which are familiar to the person skilled in the art of colour development and are generally commercially available. The matting agent may be inorganic or organic in nature. Examples of inorganic matting agents are amorphous or pyrogenic silica, silica gels and phyllosilicates, for example, hydrated magnesium silicate (talcum). The inorganic matting agents may be present in untreated form or in a form surface-treated with organic compounds, for example, with suitable grades of wax, or also with inorganic compounds. Examples of organic matting agents are Al, Zn, Ca or Mg stearate, waxy compounds, such as for example micronized polypropylene waxes, together with is urea/formaldehyde condensation products.

The matting agents may be used alone or in a combination of two or more matting agents.

The solid colour pigments used in the method according to the invention comprise conventional inorganic and/or organic absorption pigments, as are used in coating production. Examples of inorganic or organic colouring pigments are titanium dioxide, iron oxide pigments, carbon black, azo pigments, phthalocyanine pigments, quinacridone, or pyrrolopyrrole pigments. Examples of effect pigments comprise platelet-like pigments which besides colour imparting a substrate additional optical properties as angle-dependent colour and lightness travel and visual texture. The palette of effect pigments is diverse and can be divided into interference and mirror-like reflective pigments.

This disclosure is also directed to a colour recipe produced by the method disclosed herein.

This disclosure is further directed to a coating produced based on the colour recipe produced by the method of this invention. The coating can be an OEM automotive coating, a refinish coating, any other industrial coating or a combination thereof.

The method of the present invention can advantageously be used in all areas of application, where matt colour standards, in particular matt solid colour standards have to be developed or respective batches have to be shaded as, for example, in automotive and industrial coatings applications. In automotive coatings the method can be used for OEM coatings as well as refinish coatings as, e.g., in colour laboratories, in refinish body shops, in the paint manufacturing process, and in standardisation of paints. The method is applicable to matt colour standards, in particular to matt solid colour standards of unknown or of known pigmentation.

Figure 5:
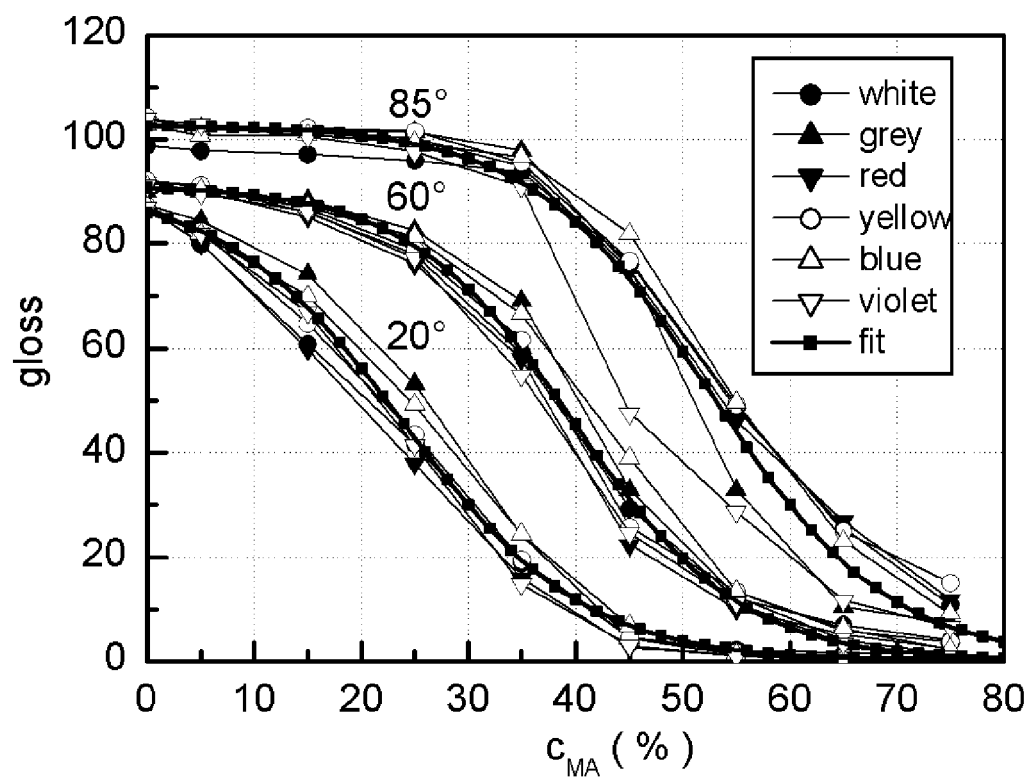
FIG. 5 shows the variation of surface gloss according to DIN 67530 for a typical solvent-based refinish mixing system at three different angles and for several chromatic and achromatic samples with matting agent content along with the model functions fitted to the experimental data (MA=matting agent).

The main advantage of the process of the present invention is that an integrating sphere colour measurement instrument, e.g. a d/8°-spectrophotometer, is capable of generating gloss information for the three standard measurement geometries of typical gloss measurement devices (20°, 60°, and 85°; see FIG. 3), in addition to the spectral information. Therefore, the functionality of the integrating sphere spectrophotometer is extended considerably, since now in a practical application (for instance in the colour tools used in refinish body-shops) it can replace the gloss-meter, which is needed in this type of application when utilising spectrophotometers is equipped with a collimated 45°/0° measurement geometry. The obtained MAA=f(gloss) gloss profiles (for example, as depicted in FIG. 5) can now be used for both types of colour measurement instruments, colour measurement instruments with d/8° geometry and colour measurement instruments with 45°/0° geometry.

The following Examples illustrate the invention in greater detail:

EXAMPLES

A first step in using the method of the present invention in colour development is to calibrate the optical behaviour of all colorants of a colorant system using an appropriate mixture model like the Schuster-Kubelka-Munk theory or its variants and to determine the universal gloss=$f(c_{MA})$ functions between gloss and matting agent (MA) content for the recommended gloss angle geometries.

FIG. 5 displays such universal functions derived for a selection of colorants (solid pigments) of a solvent-based refinish mixing system for all three angles of light incidence (20°, 60°, 85°) recommended in DIN 67530. A commercial gloss-meter has been used for carrying out the measurements. The most striking result of the plot is the almost universal functional behaviour of the gloss vs. matting agent content for the 20° and 60° angles. At the 85° angle a slightly wider spread of the curves is obvious. Fitting the gloss=$f(c_{MA})$ to a model function this data set would certainly lead to the least accurate function of the three. When comparing the variance of the curves the 20° and 60° angle results seem to be fairly competitive in deriving the matting agent content. The maximum error $\Delta c_{MA,max}$ of the 20° gloss=$f(c_{MA})$-function is approximately 4.3%, and for the remaining two angles $\Delta c_{MA,max}$ is about 3.1% for the 60° angle and 10.6% for the 85° angle. However, in view of the variability of the matting agent content in real colour shades predominantly covering the concentration range 25-65% and the highest sensitivity of the gloss=$f(c_{MA})$ curves, the 60° function is superior to the 20° function in accuracy. Below $\Delta c_{MA,max}$=30%, the 20° function exhibits a higher sensitivity than the 60° function. To achieve the most accurate results in the entire concentration range, a combination of both universal functions of the 20° and 60° angles is recommended in this specific example.

For interpolation purposes the experimentally determined calibration data have been described by an appropriate model function representing the data to a sufficient degree of accuracy. From the sets of gloss functions the maximum variance on the is abscissa can be estimated for any given gloss value. The maximum error $\Delta c_{MA,max}$ to be expected amounts to 7% for the 20° angle, 6% for the 60° angle, and 10% for the 85° angle. In view of the fact that the majority of formulas fall into the range of 25%≤$C_{MA}$≤65%, the gloss angle of 60° seems to be the best measuring geometry, since the range of highest dynamic falls within the same concentration interval.

Two semi-glossy colour shades from the RAL-system (RAL 3000, RAL 7005), representing a well-accepted and typical collection of colour standards in industrial applications, have been selected to show the efficiency of the method of the invention. The experimentally determined reflectance functions of the two selected colour standards within the visible spectral range are depicted in FIG. 10. The commercial measurement instrument used for the colour development was equipped with a d/8° measurement geometry and could be operated in the specular included (SPIN) and excluded (SPEX) modes. It was the same instrument as used to determine the calibration function. The gloss values have been measured at the three recommended angles of 20°, 60°, and 85° using the same commercial gloss-meter (see Table II) that had been used to determine the calibration function. Both colour standards have been subsequently processed through the standard procedure of colour development using a set of optical material parameters (wavelength-dependent scattering and absorption coefficients) derived from a set of glossy calibration panels. After identifying the appropriate pigmentation of the optimised recipe the formulation is sprayed out, re-measured and corrected in further steps (if necessary) using an efficient recipe correction algorithm.

The calibration curve of the pair of instruments used (gloss-meter=micro TRI-gloss instrument of Byk-Gardner; colour measurement instrument=SP64 of X-Rite) is shown in FIG. 11.

The first example shows the match prediction and correction results of the semi-glossy orange RAL 3000 standard taken from the RAL 840-HR register. The formulation used to match the standard comprises the matting agent and five colorants (pigments): two red, orange, and magenta colorants for adjusting the colour, and a white desaturant to adjust the lightness. The colour shade has been formulated without adding a carbon black pigment. All ingredient amounts are specified in Table I. As can be seen from Tab. II the residual colour difference between on-load position and colour standard is already within target zone, while is concerning the surface texture the sample obviously is too matt. An added correction step does not improve the colour position of the match further, but the gloss level is adjusted properly so that the match of the RAL3000 standard can be released.

In the second example the formulation selected to match the semi-glossy green RAL 7005 standard, also taken from the RAL 840-HR register, is similar complex. Besides the matting agent also five colorants (pigments) have to be used to achieve an acceptable spectral match: two yellow pigments and a blue one for adjusting the colour, and black and white desaturants to adjust the lightness. All ingredient amounts have been collected in Tab. I for all predicted and corrected formulations. Concerning the colour position only after the second correction step the match is close enough to the RAL 7005 colour standard (see Table II). Since the adjusted gloss level of the match is also close to the corresponding property of the standard the match can be released.

The test results, which have been collected in Tables I and II, can be summarised as follows: (i) colour differences of the on-load positions vary between 0.3 to 2.3 $\Delta E94$ units, (ii) first correction steps lead to a significant improvement of colour position, (iii) the level of surface gloss could be adjusted quite precisely using the outlined calibration function, and (iv) the convergence properties are comparable to those generally observed for glossy solid colours thereby indicating that in case of matt-finished solid colours no additional tinting steps (on the average) are needed in the colour development process.

TABLE I

Colour development information for two test examples (RAL 3000 and RAL 7005). The on-load formula represents the first match. The last column specifies the first corrected formula (MA—matting agent).

| Standard | Ingredients | On-load Formula (%) | $1^{st}$ Correction Step (%) | $2^{nd}$ Correction Step (%) |
|---|---|---|---|---|
| RAL 3000 | White | 3.37 | 3.95 | — |
| | Red1 | 15.97 | 15.67 | — |
| | Red2 | 5.06 | 5.97 | — |
| | Orange | 28.53 | 33.7 | — |
| | Magenta | 11.37 | 13.44 | — |
| | MA | 35.7 | 27.27 | — |
| RAL 7005 | White | 30.09 | 30.67 | 32.6 |
| | Black | 10.93 | 12.89 | 12.45 |
| | Yellow1 | 5.01 | 5.11 | 5.32 |
| | Yellow2 | 2.79 | 2.09 | 2.02 |
| | Blue | 0.1 | 0.27 | 0.3 |
| | MA | 51.08 | 48.97 | 47.31 |

TABLE II

Experimental results (colour and gloss information) of the two test colour shades taken from the RAL system that have been worked out in a solvent-based Refinish paint line for passenger cars (STD—standard; R—recipe; CR—corrected recipe). In the three columns specifying the surface gloss the gloss numbers in bold (second row, respectively) are derived from the generalised instrument profile, while those depicted in normal mode (first row, respectively) have been determined experimentally by means of a gloss-meter.

| | | $L^*$ $\Delta L^*$ | $a^*$ $\Delta a^*$ | $b^*$ $\Delta b^*$ | $C^*$ $\Delta C^*$ | $h_{ab}$ $\Delta H^*$ | $\Delta E^*(76)$ | $\Delta E^*(94)$ | Gloss (20°) | Gloss (60°) | Gloss (85°) |
|---|---|---|---|---|---|---|---|---|---|---|---|
| RAL 3000 | STD | 35.0 | 52.30 | 41.70 | 66.90 | 38.60 | — | — | 13.2 12.8 | 58.9 50.5 | 88.5 87.4 |
| | 1R | −0.07 | 0.51 | 0.73 | 0.85 | 0.25 | 0.89 | 0.26 | 25.1 3.1 | 34.6 25.7 | 78.9 66.8 |
| | 1CR | −0.14 | 0.22 | 0.68 | 0.60 | 0.39 | 0.73 | 0.29 | 36.8 15.5 | 77.1 53.9 | 95.3 89.3 |
| RAL 7006 | STD | 44.9 | −1.70 | 2.90 | 3.40 | 120.70 | — | — | 2.1 2.5 | 18.7 22.5 | 36.2 62.6 |
| | 1R | 1.72 | 0.45 | 1.45 | 1.16 | −0.98 | 2.29 | 2.29 | 1.7 1.3 | 15.6 14.2 | 50.9 47.6 |
| | 1CR | −1.25 | 0.11 | −0.16 | −0.19 | −0.01 | 1.27 | 1.26 | 1.9 1.5 | 17.4 15.8 | 55.0 51.0 |
| | 2CR | 0.47 | 0.04 | −0.10 | −0.10 | 0.01 | 0.48 | 0.48 | 3.2 3.2 | 24.9 26.1 | 58.6 67.4 |

TABLE III

| Instrument | STDDEV | | |
|---|---|---|---|
| | 20° | 60° | 85° |
| SP64 | 12.19 | 6.46 | 7.15 |
| SF600 | 14.10 | 6.51 | 5.82 |
| Color-Eye 7000 | 3.60 | 2.99 | 5.00 |

The invention claimed is:

1. A method for producing a colour recipe for a matt colour standard, said method comprising the steps of:
   A) experimentally determining reflection spectra R(exp) of the colour standard, comprising a first reflection spectrum and a second reflection spectrum, utilizing an integrating sphere colour measurement instrument configured to obtain said first reflection spectrum and said second reflection spectrum, wherein said first reflection spectrum is obtained at
   (A1) d/8°—geometry or 8°/d—geometry with the specular component included, and said second reflection spectrum is obtained at
   (A2) d/8°—geometry or 8°/d—geometry with the specular component excluded;
   B1) calculating a recipe for the matt colour standard based on the experimentally determined reflection spectra R(exp), wherein the experimentally determined reflection spectrum R(exp) with the specular component included (A1), which has been corrected for the specular component, is matched by using the optical material parameters of the solid pigments of an available colorant system for the preparation of glossy colour shades, so obtaining a colour recipe specifying the nature of the pigments and the concentrations thereof, or
   B2) comparing the experimentally determined reflection spectrum R(exp) with the specular component included (A1), which has been corrected for the specular component, with reflection spectra associated to colour recipes of a colour recipe database for glossy colour shades and identifying from said colour recipe database a stored reflection spectrum which comes closest to the experimentally determined reflection spectrum R(exp) of the matt colour standard, as well as identifying the associated colour recipe;
   C) converting reflection spectra data of the experimentally determined reflection spectra R(exp) of the matt colour standard to gloss values by:
   C1) acquiring a difference reflection spectrum ΔR of the experimentally determined reflection spectrum R(exp) with the specular component included (A1) and the experimentally determined reflection spectrum R(exp) with the specular component excluded (A2), both obtained utilizing the integrating sphere colour measurement instrument, and
   C2) determining the gloss values corresponding to said difference reflection spectrum ΔR with the assistance of previously prepared calibration curves for the available colorant system, whose curves represent the functional relationship between the difference reflection spectrum ΔR and the gloss values measured at one or more gloss angles,
   D) producing the colour recipe for the matt colour standard by converting the gloss values obtained to the amount of matting agent with the assistance of previously prepared calibration curves for the available colorant system, whose curves represent the gloss values measured at one or more gloss angles as a function of the amount of at least one matting agent in colour recipe, wherein the colour recipe produced is at least based on the colour recipe of B1) or B2), and the amount of at least one matting agent, producing a coating composition based on the colour recipe of D) for the matt colour standard; and applying the coating composition to a substrate to form a coating layer.

* * * * *